(12) United States Patent
Ren et al.

(10) Patent No.: US 10,987,172 B2
(45) Date of Patent: Apr. 27, 2021

(54) ADAPTIVE IMAGE REGISTRATION FOR OPHTHALMIC SURGERY

(71) Applicant: NOVARTIS AG, Basel (CH)

(72) Inventors: Hugang Ren, Cypress, CA (US); Lingfeng Yu, Rancho Santa Margarita, CA (US)

(73) Assignee: Alcon Inc.

( * ) Notice: Subject to any disclaimer, the term of this patent is extended or adjusted under 35 U.S.C. 154(b) by 494 days.

(21) Appl. No.: 15/837,406

(22) Filed: Dec. 11, 2017

(65) Prior Publication Data

US 2018/0168737 A1    Jun. 21, 2018

Related U.S. Application Data

(60) Provisional application No. 62/434,874, filed on Dec. 15, 2016.

(51) Int. Cl.
*A61B 34/20* (2016.01)
*A61B 3/14* (2006.01)
(Continued)

(52) U.S. Cl.
CPC .............. *A61B 34/20* (2016.02); *A61B 3/005* (2013.01); *A61B 3/0025* (2013.01); *A61B 3/0058* (2013.01); *A61B 3/10* (2013.01); *A61B 3/102* (2013.01); *A61B 3/13* (2013.01); *A61B 3/132* (2013.01); *A61B 3/14* (2013.01); *A61B 90/36* (2016.02); *A61F 9/007* (2013.01); *A61B 90/20* (2016.02); *A61B 2034/2055* (2016.02); *A61B 2034/2065* (2016.02);
(Continued)

(58) Field of Classification Search
CPC ........... A61B 3/102; A61B 3/13; A61B 90/20; A61B 2090/3735; A61F 2009/00851
See application file for complete search history.

(56) References Cited

U.S. PATENT DOCUMENTS 7,231,076 B2    6/2007    Fu et al.
2008/0095465 A1    4/2008    Mullick et al.
(Continued)

OTHER PUBLICATIONS

Ho et al., "Optical coherence tomography in the detection of retinal break and management of retinal detachment in morning glory syndrome", ACTA Ophthalmologica Scandinavica, 2006, 84, pp. 225-227.

(Continued)

*Primary Examiner* — Jason M Ip
(74) *Attorney, Agent, or Firm* — Joseph Weatherbee, Esq.

(57) ABSTRACT

An ophthalmic surgical system includes a first imaging system configured to generate a first image of an eye, a second imaging system configured to generate a second image of the eye, and an image registration system to receive the first image generated by the first imaging system, receive the second image generated by a second imaging system, track a location of a distal tip of a surgical instrument in the first image, define a priority registration region in the first image, register the priority registration region in the first image with a corresponding region in the second image, and update the registration of the priority registration region in the first image with the corresponding region in the second image in real time, without registering portions of the first or second images that are outside the registration regions.

16 Claims, 6 Drawing Sheets

(51) Int. Cl.
  *A61F 9/007* (2006.01)
  *A61B 3/10* (2006.01)
  *A61B 3/13* (2006.01)
  *A61B 90/00* (2016.01)
  *A61B 3/00* (2006.01)
  *A61F 9/008* (2006.01)
  *A61B 90/20* (2016.01)
  *A61B 90/50* (2016.01)

(52) U.S. Cl.
  CPC ... *A61B 2090/364* (2016.02); *A61B 2090/365* (2016.02); *A61B 2090/3612* (2016.02); *A61B 2090/371* (2016.02); *A61B 2090/372* (2016.02); *A61B 2090/374* (2016.02); *A61B 2090/376* (2016.02); *A61B 2090/3735* (2016.02); *A61B 2090/502* (2016.02); *A61F 2009/00851* (2013.01)

(56) References Cited

U.S. PATENT DOCUMENTS

| | | |
|---|---|---|
| 2008/0100612 A1 | 5/2008 | Dastmalchi et al. |
| 2012/0184846 A1 | 7/2012 | Izatt et al. |
| 2013/0039550 A1* | 2/2013 | Blum ................ G06T 7/30 |
| | | 382/128 |
| 2013/0336559 A1 | 12/2013 | Kersting et al. |
| 2015/0173644 A1 | 6/2015 | Ren et al. |
| 2015/0206309 A1 | 7/2015 | Yang |
| 2015/0342460 A1 | 12/2015 | Izatt et al. |
| 2016/0183779 A1 | 6/2016 | Ren et al. |

OTHER PUBLICATIONS

Kawazoe et al., "Evaluation of a partial retinal surface tear by optical coherence tomography", Clinical Ophthalmology, May 31, 2011, pp. 733-734.

Li et al., "Registration of OCT fundus images with color fundus photographs based on blood vessel ridges", Optics Express, Jan. 17, 2011, vol. 19, No. 1, pp. 7-16.

Perez-Rovira et al., "RERBEE: Robust Efficient Registration via Bifurcations and Elongated Elements Applied to Retinal Fluorescein Angiogram Sequences", IEEE Transactions on Medical Imaging, Jan. 1, 2012, vol. 31, No. 1, pp. 140-150.

Wong et al., "Dye Extrusion Technique (DE-Tech)", Retina, The Journal of Retinal and Vitreous Diseases, 2009, vol. 29, No. 4, pp. 492-496.

* cited by examiner

ADAPTIVE IMAGE REGISTRATION FOR OPHTHALMIC SURGERY

FIELD

The present disclosure relates generally to medical imaging, and more particularly to ophthalmic surgical imaging.

BACKGROUND

Image-guided surgery can provide improved safety and patient outcomes compared with conventional surgery. For example, medical practitioners performing optical coherence tomography (OCT) guided macular surgery or fluorescein angiography (FA) guided laser photocoagulation utilize guidance images to enhance precision and insight during surgical procedures.

Guidance images may be acquired pre- or intra-operatively, and are typically viewed in conjunction with live video images of the surgeon's field of view. Accurate real-time image registration between guidance images and the current field of view is important so that a surgeon can confidently rely on the guidance images in real time during a procedure.

For example, certain ophthalmic surgical procedures require the cutting and/or removal of the vitreous humor, a transparent jelly-like material that fills the posterior segment of the eye. Cutting and removal of the vitreous must be done with great care to avoid traction on the retina, the separation of the retina from the choroid, a retinal tear, or, in the worst case, cutting and removal of the retina itself. Given the delicate nature of vitreoretinal surgery, it is crucial that guidance image data is registered to the field of view with both a high degree of accuracy and speed so that the surgeon may make decisions based on the images.

Image registration is challenging in part due to intensive computational demands it imposes, as the processing load required by real-time image registration makes it difficult to accurately register images at real-time speeds. There exists a need for improved image registration techniques in ophthalmic surgery.

SUMMARY

Certain embodiments include an ophthalmic imaging system comprising a first imaging system configured to generate a first image of an eye, a second imaging system configured to generate a second image of the eye, and an image registration system comprising a processor and instructions stored on a memory. The instructions are executable by the processor to cause the image registration system to receive the first image generated by the first imaging system, receive the second image generated by a second imaging system, track a location of a distal tip of a surgical instrument in the first image, define a priority registration region in the first image, the priority registration region comprising a portion of the first image within a predetermined proximity of the distal tip of the surgical instrument, register the priority registration region in the first image with a corresponding region in the second image, and update registration of the priority registration region in the first image with the corresponding region in the second image in real time as the distal tip is moved, without registering portions of the first and second images that are outside the registration regions.

In certain embodiments, the first and second images comprise first and second images of a fundus, a sclera, or an iris. The first imaging system may comprise at least one of a surgical microscope, a 2-dimensional camera, a line-scan camera, and a single detector as used in a confocal scanning ophthalmoscope. The second imaging system may comprise at least one of an Optical Coherence Tomography (OCT) imaging system and a fluorescein angiogram imaging system.

Additionally, embodiments of the system include instructions executable by the processor to cause the image registration system to generate, in real time, a display image in which the registration region in the first image is aligned with the corresponding registration region in the second image, and portions of the first or second images that are outside the registration regions are not registered. In certain embodiments, an unregistered portion of the first or second image is visually suppressed in the generated display image.

Embodiments of the system may further comprise an eyepiece or a heads-up screen configured to display the generated display image.

In certain embodiments, at least one characteristic of the priority registration region is configurable by a user. For example, a size of the priority registration region is configurable by a user.

In certain embodiments, a size of the priority registration region is dynamically adjusted based on processing load.

The location of the distal tip may be tracked using a feature-based, region-based, or motion-based object tracking algorithm.

In certain embodiments, the distal tip comprises a feature of interest selected by a system operator. The distal tip may be selected as a feature of interest prior to an imaging procedure, and the distal tip may be selected from a list of features of interest which can be tracked.

In certain embodiments, a method for registering images in an ophthalmic imaging system comprises receiving a first image generated by a first imaging system, receiving a second image generated by a second imaging system, tracking a location of a distal tip of a surgical instrument in the first image, defining a priority registration region in the first image, the priority registration region comprising a portion of the first image within a predetermined proximity of the distal tip of the surgical instrument, registering the priority registration region in the first image with a corresponding region in the second image, and updating registration of the priority registration region in the first image with the corresponding region in the second image in real time as the distal tip is moved, without registering portions of the first and second images that are outside the registration regions.

Certain embodiments of the method further comprise generating, in real time, a display image in which the registration region in the first image is aligned with the corresponding registration region in the second image, and portions of the first or second images that are outside the registration regions are not registered.

Examples of the method may include visually suppressing an unregistered portion of the first or second image. Additionally or alternatively, the method may include displaying the display image in an eyepiece or on a heads-up screen.

Embodiments of the method may include defining the priority registration region in the first image based on user input. Additionally or alternatively, the method may include dynamically adjusting a size of the priority registration region based on processing load. In certain examples, the location of the distal tip is tracked using a feature-based, region-based, or motion-based object tracking algorithm.

In certain embodiments, the method includes receiving, from a system operator, an input identifying the tool tip as a feature of interest to be tracked. The tool tip may be identified as a feature of interest prior to an imaging procedure, and the tool tip may be selected from a list of features of interest which can be tracked.

Certain embodiments may provide one or more technical advantages. For example, systems and method according to the disclosure may provide highly-accurate, high-speed image registration, in some instances without hardware modifications to the underlying imaging systems generating images to be registered. Certain embodiments improve visualization during delicate ophthalmic procedures by prioritizing image registration in the most critical regions of live video images and corresponding enhanced images (e.g., preoperative or intraoperative OCT). For example, embodiments may track the location of the tip of a surgical tool, define an image registration area in proximity to the tip, and register applicable images only within the defined area (e.g., such that registration outside the defined area is not attempted). Additionally or alternatively, embodiments may define an image registration area based on features, pathologies, or other aspects of an image. These and other advantages will be apparent to those skilled in the art in view of the present drawings and specification.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
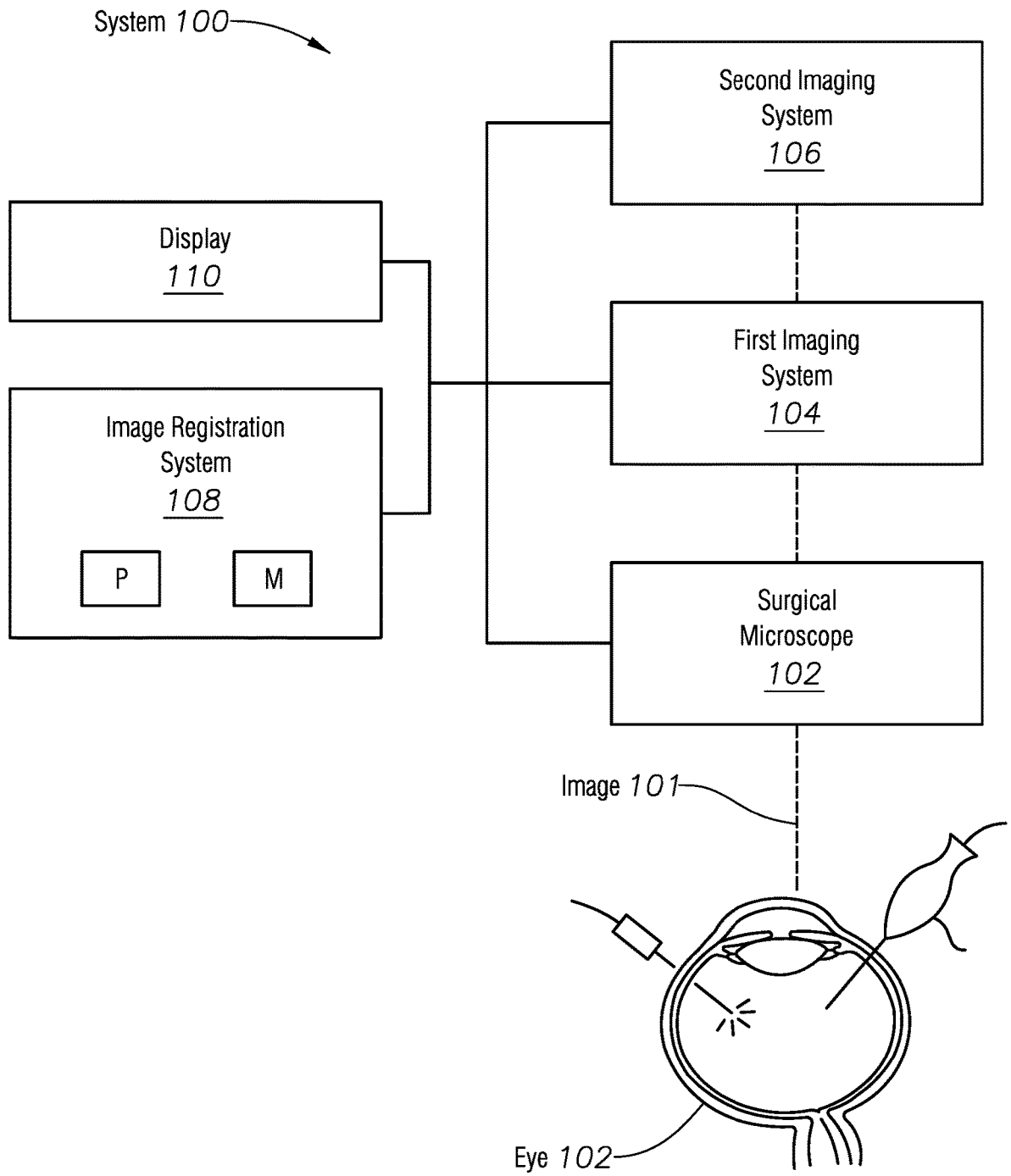
FIG. 1 illustrates an example of ophthalmic surgical visualization system for adaptive image registration, according to certain embodiments.

One skilled in the art will understand that the drawings, described below, are for illustration purposes only, and are not intended to limit the scope of applicant's disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and further modifications to the described systems, devices, and methods, and any further application of the principles of the present disclosure are contemplated as would normally occur to one skilled in the art to which the disclosure relates. In particular, it is contemplated that the systems, devices, and/or methods described with respect to one embodiment may be combined with the features, components, and/or steps described with respect to other embodiments of the present disclosure. For brevity, the numerous iterations of these combinations will not be described separately. And for simplicity, in some instances the same reference numbers are used throughout the drawings to refer to the same or like parts.

In general, the present disclosure relates to an ophthalmic surgical system capable of providing adaptive, real-time image registration based on features within the image of interest to the surgeon. Certain embodiments provide a user with a magnified image of a surgical field of view (generated, for example, by a digital video camera, line scan ophthalmoscope, or confocal-scanning ophthalmoscopes) that includes a computer-generated visual overlay corresponding to guidance image data generated by a guidance imaging system, such as an optical coherence tomography (OCT) imaging system, a fluorescence angiogram imaging system, a stereophotogrammetry imaging system, a computerized axial tomography (CAT) scan system, a magnetic resonance imaging (MM) system, or a positron emission tomography (PET) imaging system.

Certain embodiments provide real-time registration and alignment between the field of view and guidance image(s) within a surgeon's current region of interest. For example, certain embodiments include an image registration system configured to recognize the tip of a surgical tool within a video image of the surgeon's field of view and identify or define a surrounding area in proximity to the tool tip as a region of interest corresponding to a priority registration region. Other embodiments may recognize key features within the surgical area, such as a retinal break, epiretinal membrane, or retinal detachment, and identify surrounding areas as registration regions. The image registration system may prioritize registration of video and guidance imaging data in within the registration regions in order to maintain high registration accuracy in that region and facilitate real-time surgical decision-making based on guidance image data. In some embodiments, the image registration system only registers the images within the identified registration regions, and other areas of the images are not registered. This allows the image registration system to dedicate resources to registering only the most critical regions of the images.

FIG. 1 illustrates certain components of an example of ophthalmic surgical system 100 for image-guided surgery which includes surgical microscope 102, first imaging system 104, second imaging system 106, image registration system 108, and display 110, each of which may be coupled physically and/or communicatively.

Surgical microscope 102 may facilitate magnified viewing of a patient's eye 102 during a surgical procedure and may generally include eyepieces, a relay lens, magnifying/focusing optics, an objective lens, and surgical viewing optics. Each of eyepieces, relay lens, magnifying/focusing optics, objective lens, and surgical viewing optics may include any suitable optical components as understood by those skilled in the art.

Surgical microscope 102 may be coupled to one or more imaging systems to support enhanced surgical imaging, such as a first imaging system 104 and second imaging system 106. First imaging system 104 and second imaging system 106 may be optically integrated and aligned with surgical microscope 102 via suitable components (e.g., beam splitters, mirrors, etc.) to acquire images of an eye. First imaging system 104 and second imaging system 106 may comprise any imaging systems suitable for assisting with ophthalmic surgery, though they typically will provide complimentary functionality.

For example, first imaging system 104 may provide a magnified view of tissues of eye 102 within a surgeon's desired field of view. The magnified images provided by such a system may be 2D or 3D, preoperative or live intra-operative (real-time) images of eye tissue (e.g., fundus, iris, etc.), and may comprise discrete still photographs of the patient's eye 102 or a continuous video stream of the patient's eye 102. In certain examples, the system may provide multiple image frames that can be processed and modified by other components of system 100. Examples of such imaging systems 104 include digital video cameras, line scan ophthalmoscopes, and confocal-scanning ophthalmoscopes.

In certain embodiments, second imaging system 106 may provide guidance images to supplement the tissue images provided by the first imaging system 104 and assist in the surgical procedure. Guidance images may be 2D or 3D, preoperative or intra-operative images of any aspect of eye 102, and may comprise discrete still photographs of the patient's eye 102 or a continuous video stream of the patient's eye 102. In certain examples, the imaging system may provide multiple image frames that can be processed and modified by other components of system 100. Examples of such second imaging systems 106 include OCT imaging systems, fluorescence angiogram imaging systems, stereo photogrammetry imaging systems, computerized axial tomography (CAT) scan systems, magnetic resonance imaging (Mill) systems, and positron emission tomography (PET) imaging systems.

The imaging systems discussed above are known in the field of ophthalmic surgery, and their architecture and operation are not discussed in detail for brevity. It is noted, however, that in various embodiments of system 100, first imaging system 104 and second imaging system 106 may include any suitable imaging systems, including any combination of particular imaging systems described herein. Further, one or both imaging systems may be integrated with or mounted to surgical microscope 102 in any suitable manner, and may comprise probe-based imaging systems. In a typical embodiment, first imaging system 104 comprises a digital video cameras, line scan ophthalmoscope, or confocal-scanning ophthalmoscope, and second imaging system 106 comprises an OCT or fluorescence angiogram imaging system. In example system 100, first imaging system 104 comprises a digital video camera and second imaging system 106 comprises an OCT imaging system. However, it is understood that that alternative imaging systems are within the scope of the present disclosure, and the first and second imaging systems 104, 106 may comprise any suitable combination of imaging systems.

System 100 further includes an image registration system 108 and display 110. Image registration system 108 receives images generated by first imaging system 104 and second imaging system 106 and generates 2D or 3D video image data to simultaneously present video microscope and guidance images to a surgeon as a composite image on display 110. For example, guidance images (e.g., OCT images) may be processed and output as a semitransparent overlay aligned with the visible structures in a video microscope image viewed by the surgeon via display 110 (as shown, for example, in FIGS. 3-5). In such embodiments, alignment between the guidance images and the actual structures of the eye may be achieved using an adaptive image registration process that continuously analyzes and aligns the images in real time. Example adaptive image registration processes in accordance with certain embodiments are discussed in additional detail below.

Image registration system 108 may include any suitable combination of hardware, firmware, and software configured to register and display images generated by the first and second imaging systems. In certain embodiments, registration system 108 includes a processor coupled to a memory (denoted "P" and "M" in FIG. 1, respectively). The processor may include one or more CPUs, microprocessors, field-programmable gate arrays (FPGAs), controllers, ASICs, DSPs, or equivalent components. The memory may include volatile or non-volatile memory including magnetic media, optical media, random access memory (RAM), read-only memory (ROM), removable media, or equivalent components. The memory may store instructions for software programs and algorithms that, when executed by the processor, perform the functions of image registration system 108 described herein. As used in the claims, the terms "processor," "memory," "instructions," and the like refer to classes of structures that known to those skilled in the art, and are to be understood as denoting structural rather than functional elements of the disclosed system.

Display 110 may include any suitable device for displaying images, including one or more eye pieces, a display screen, heads-up display, a one-dimensional or two-dimensional display array, a projector, a holographic display, viewing goggles or glasses, etc. Display 110 may display 2D or 3D images received from image registration system 108, first imaging system 104, second imaging system 104, and/or surgical microscope 102 in various embodiments.

Real-time image registration is computationally-demanding, requiring a great number of calculations performed continuously to align high-resolution images with requisite accuracy. It is difficult to simultaneously achieve high accuracy and speed, and conventional image registration systems often suffer from poor responsiveness, delay, jitter, and misalignment, as shown in FIG. 2.

Figure 2:
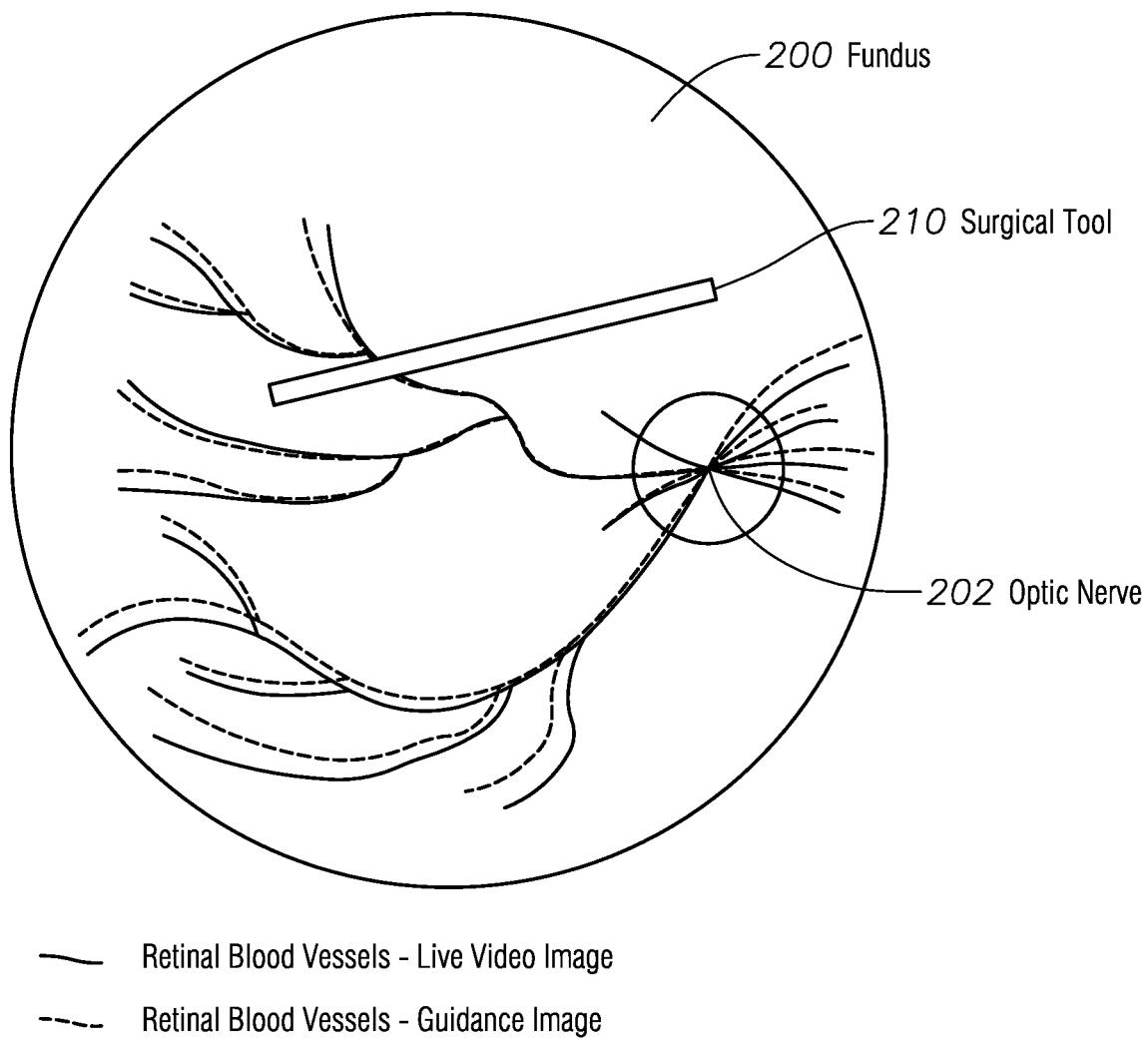
FIG. 2 illustrates a registered image generated by a conventional image registration system.

FIG. 2 depicts an image of fundus 200 generated by a video microscope. Visible within the fundus image 200 are a surgical tool 210, optic nerve 202, and retinal blood vessels. As shown in the key at the bottom of FIG. 2, retinal blood vessels in the real-time video microscope image are depicted as solid lines. Fundus image 200 also includes an overlay image of retinal blood vessels generated by a guidance imaging system (e.g., an OCT system), represented by dashed lines.

As seen in FIG. 2, the solid lines and dashed lines are poorly aligned in many parts of fundus image 200, including areas near surgical tool 201. This misalignment indicates inaccurate registration and is a result of the conventional registration system's inability to meet the processing demands of the image registration program. The inaccurate result is highly problematic; fast and accurate image registration between the guidance image and the surgeon's view of the eye tissue is critical during ophthalmic surgical procedures. This is particularly true in procedures such as vitreoretinal surgery, which is typically performed on a patient who remains awake. Inaccurate, slow, or jittery image registration can lengthen the time of surgery (by forcing a surgeon to slow down his or her movements and pause to wait for alignment), make delicate surgeries more difficult and dangerous (by providing inaccurate information about the location of blood vessels), and lead to medical complications and poor outcomes.

Embodiments of system 100 address this using an improved image registration system 108 configured to perform an adaptive image registration process for high-speed, highly-accurate registration of the most critical areas of the images. In particular, registration system 108 may receive and analyze images received from the first or second imaging systems to dynamically identify key features (e.g., a surgical tool tip, a tissue feature such as an optic nerve, a pathology, etc.). Based on these features, registration system 108 defines priority registration areas/regions in proximity to those features in real time, and prioritizes registration the registration areas in the images. In certain embodiments, registration system 108 actively limits or restricts image registration to the defined registration areas in order to efficiently allocate processing resources to registering the most important areas of the image. Accordingly, registration system 108 implements an adaptive process (which may track key features, such as a surgical tool tip, in real time) that efficiently allocates image processing resources to the critical areas within a surgical view, increasing the accuracy and speed of registration in those areas. In certain examples, these improvements can be realized as an in a software upgrade to a conventional registration system (converting it to an improved registration system 108), thereby realizing gains in performance and efficiency without modifying hardware.

Figure 6:
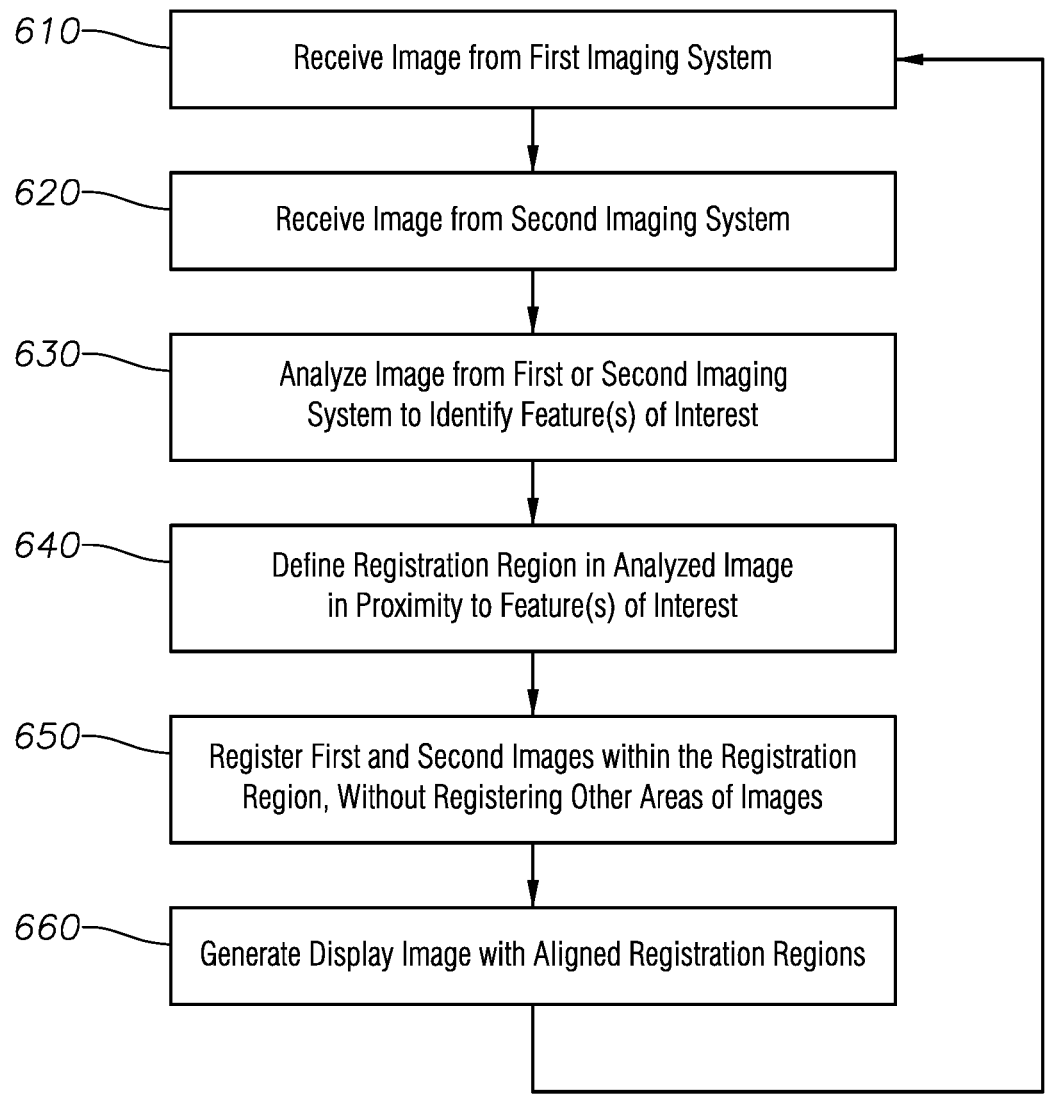
FIG. 6 is a flow chart illustrating steps performed by an improved image registration system, according to certain embodiments.

FIG. 6 illustrates a flow chart describing steps in one example of an adaptive image registration process in accordance with certain embodiments. As noted above, image registration system 108 includes a processor, memory, and instructions stored in memory. The instructions comprise software that, when executed by a processor, causes registration system 108 to perform the adaptive registration process described in FIG. 6.

In particular, at step 610, registration system 108 receives an image or series of images (e.g., a video feed) from the first imaging system 104 (e.g., a video microscope). The images received from the first imaging system may comprise fundus images (see, e.g., FIGS. 3-4), images of external eye features (see, e.g., FIG. 5), or other tissues within a surgical field of view.

At step 620, registration system 108 receives an image or series of images (e.g., preoperative or intraoperative OCT images) from the second imaging system 104 (e.g., a spectral-domain or swept-source OCT system). The images received from the second imaging system may comprise guidance images related to the tissues depicted in the image(s) received from the first imaging system 104. Although FIG. 6 depicts receiving images from the first imaging system before the second imaging system, the order may be reversed.

At step 630, registration system 108 analyzes one of the received images or sets of images to identify one or more features or regions of interest, such as the location of the tip of a surgical instrument. Additionally or alternatively, registration system 108 may identify biological features such as blood vessels, pathologies, a retinal break, epiretinal membrane, or retinal detachment as feature(s) of interest.

In certain examples, registration system 108 may allow a system operator to configure or select (via a user interface, voice command, motion/gesture, or other input) one or more types of features (e.g., tool tip, pathologies, features, etc.) to be identified and tracked as features of interest, either alone or in combination. Such selections may be made before an imaging procedure or on the fly during a procedure.

Image registration system 108 may use any suitable image processing algorithm(s), including feature-based, region-based, or motion-based object tracking algorithms, to identify such features or regions. For example, certain embodiments may utilize feature recognition or extraction techniques and/or motion-based object tracking and image processing algorithms (e.g., edge detection, corner detection, blob detection, blob extraction, ridge detection, scale-invariant feature transform, motion detection, background subtraction, frame difference, optical flow, thresholding, template matching, Hough transform, etc.) to analyze received images and identify features within the images. In certain embodiments, registration system 108 may use such techniques to identify and track the location of a tool tip within a surgical image in real time. Certain examples may be specifically configured to recognize and track a distinctive marker located at the tip of the surgical tool, as described in U.S. Patent Pub. No. 2015-0173644A1, which is incorporated by reference herein in its entirety.

Based on the identification of feature(s) of interest, image registration system 108 at step 640 defines one or more priority registration areas in proximity to the feature(s). In certain embodiments, the registration area may be an area within a predetermined distance (e.g., radius) from an identified feature.

In various embodiments, the size of the registration areas may be static or dynamic, and may be configured by a system operator before or during a procedure. The size of the registration area may be an absolute value (e.g., a radial value) or a relative value (e.g., a particular portion of the field of view). In certain embodiments, image registration system 108 may automatically adjust the size of the priority registration area based on processing load. For example, registration system 108 may receive an indication of a current and/or anticipated processing load such as processor queue or processor utilization data. Based on such an indication, registration system 108 may increase or decrease the size of the registration area to a maximum size which allows registration of the registration area with requisite accuracy and speed. Likewise, registration system 108 may dynamically increase or decrease the size of the registration area as necessary to maintain desired performance in the registration area as processing load varies.

After a registration area is defined, at step 650 registration system 108 executes a registration algorithm to register the first and second images within the defined registration area(s). In some embodiments, registration system 108 performs this step without registering areas of the images outside the registration areas. That is, registration of the first and second images is, in certain examples, actively confined or restricted to the area(s) defined at step 640 in proximity to the feature(s) of interest, so that processing resources are not spent registering areas of the images in lower priority areas.

Embodiments of registration system 108 may use any suitable image registration technique to correlate first and second images to one another, such that points in the two images which correspond to the same anatomical points are mapped to each other in a display image. Example image registration algorithms may utilize intensity-based algorithms or feature-based algorithms to identify differences in images taken at different times and/or relate information in different types of images. Using known techniques, applicable portions of the first and second images may be translated, rotated, scaled, etc. based on features in or characteristics of the images. For example, first and second images may be registered by extracting features or identifying landmarks in the images, determining the distance between the features or landmarks, and minimizing the distance in a registered image. In certain embodiments, registration system 108 may execute an image registration algorithm which includes vessel segmentation, bifurcation and creation of elongated elements, and pairwise registration. Example image registration techniques include: Procrustes point alignment, iterative closest point (ICP), Chamfer distance matching, fuzzy correspondence, pixel-based registration, Voxel-based registration, dense field methods, linear spatial transformations, intensity mappings, and partitioned image uniformity.

At step 660 registration system 108 generates and outputs a display image in which the first and second images are registered in the priority registration region(s), but are not registered outside those regions. The generated image may comprise a composite image which includes aspects of both the first and second image aligned within the priority registration region. The composite may comprise an overlay (as shown in the examples of FIGS. 3-5), a window, or any suitable combination of aspects of the first and second images which provide a surgeon or system operator with the desired composite view.

Figure 3:
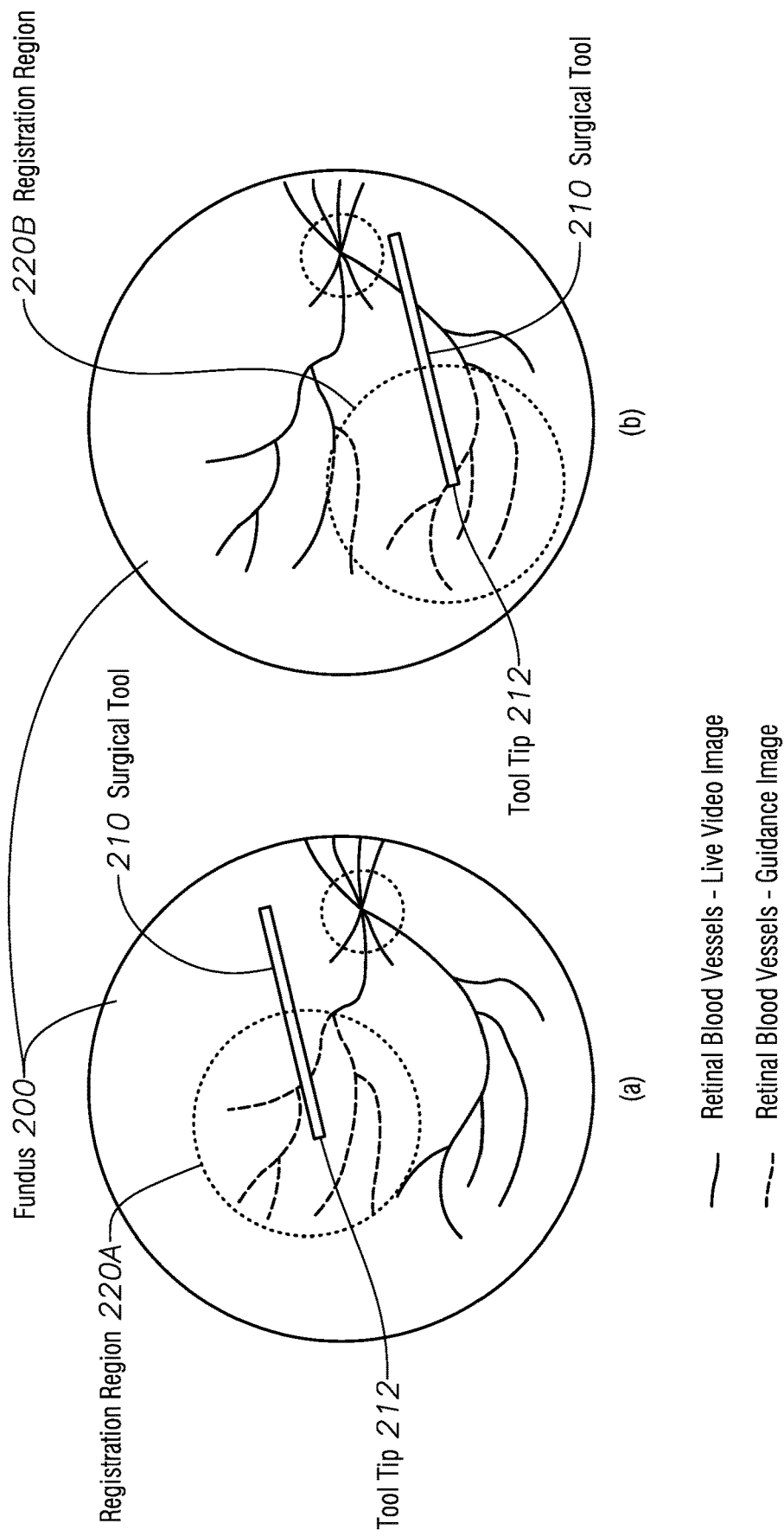
FIG. 3 illustrates a registered image generated by an improved image registration system, according to certain embodiments.
Figure 4:
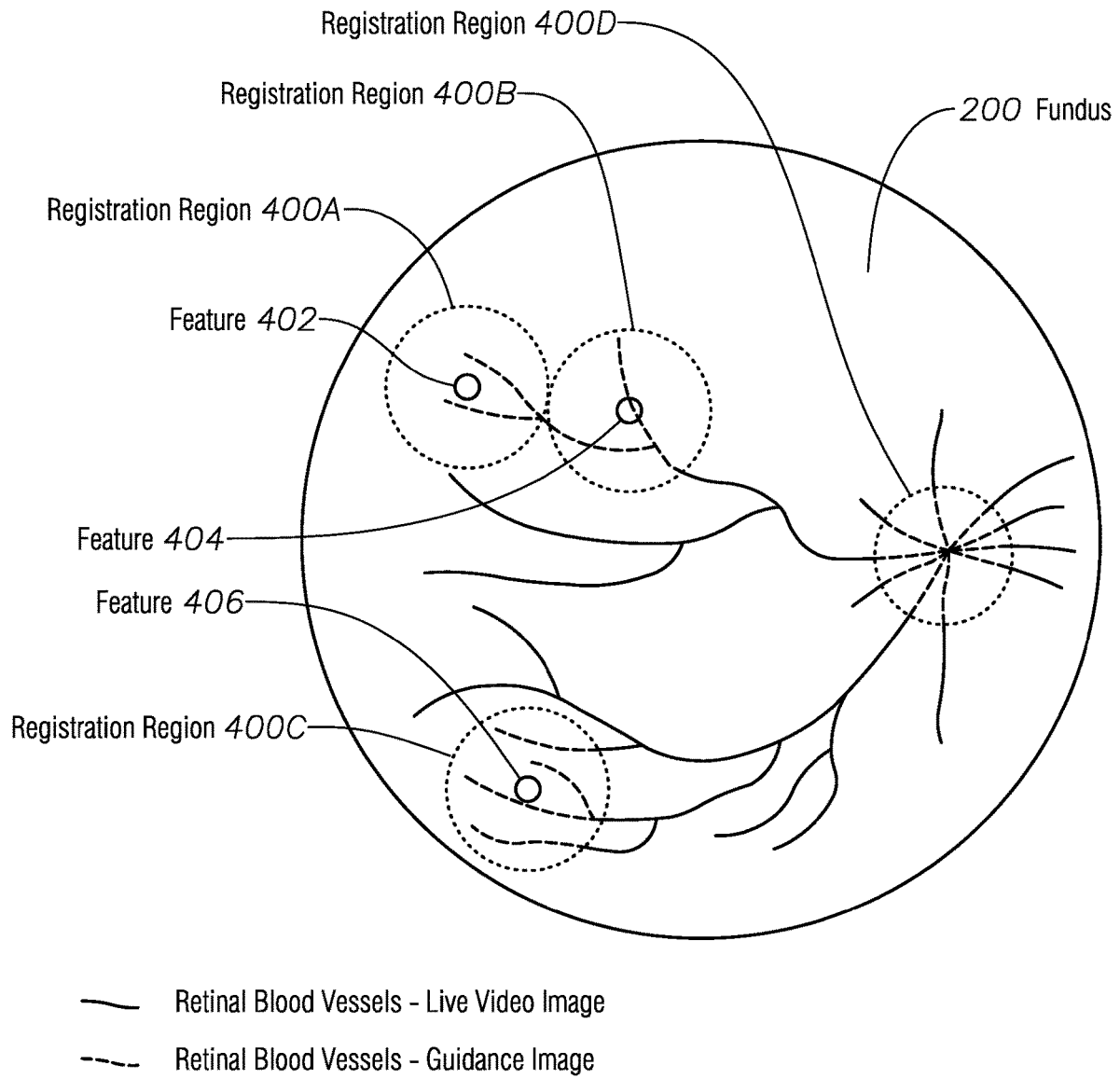
FIG. 4 illustrates a registered image generated by an improved image registration system, according to certain embodiments.
Figure 5:
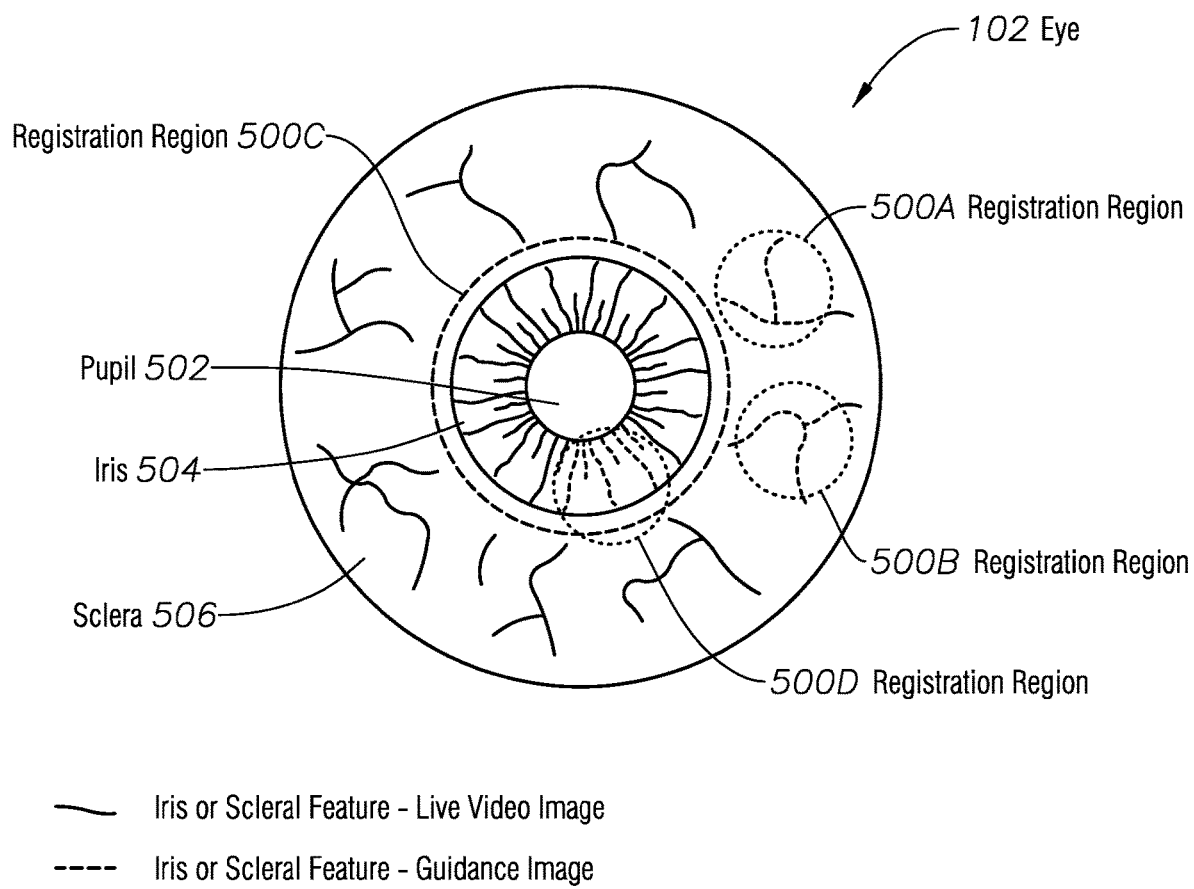
FIG. 5 illustrates a registered image generated by an improved image registration system, according to certain embodiments.

FIGS. 3-5 depict registered images which may be generated according to the process described above with respect to FIG. 6.

In particular, FIG. 3 depicts two fundus images (a) and (b) of fundus 200 generated by a first imaging system 104 (e.g., a video microscope). Retinal blood vessels in the live video image generated by the first imaging system 104 are depicted as solid black lines, while retinal blood vessels in the guidance image overlay generated by the second imaging system 106 are depicted as dashed lines. In this example, registration system 108 receives and analyzes the live video image corresponding to (a) on the left side of FIG. 3, identifying the tip 212 of surgical tool 210 as a feature of interest using feature-based, region-based, or motion-based object tracking algorithm(s). This process is executed in real time so that, as the tip of surgical tool 210 moves to another position shown in image (b) on the right side of FIG. 3, registration system 108 tracks the location of tool tip 212. As registration system 108 tracks the location of tool tip 212, priority registration regions 220A and 220B are dynamically defined by registration system 108 to encompass the area within a particular radial distance of tool tip 212. In certain examples, the size of the registration system 108 (e.g., a radial distance from the tool tip 212) may be dynamically defined and modified based on an indication of current or anticipated processing load, such as queue length or processor utilization.

Accordingly, when tool tip 212 is in the position depicted in (a) on the left of FIG. 3, registration system 108 quickly and accurately registers the first and second images within the priority registration region 220A (alignment of dashed and solid lines indicates accurate registration). Here, the retinal blood vessels (and/or other features) shown in the live video image generated by the first imaging system are accurately registered to the same retinal blood vessels (and/or other features) depicted in the guidance image (e.g., an OCT image), though other portions of the fundus images are not registered. Indeed, registration system 108 does not attempt to register portions of the first and second images outside registration region 220A.

When tool tip 212 moves to the position depicted in (b) on the right of FIG. 3, registration system 108 quickly and accurately registers the first and second images within the priority registration region 220B (alignment of dashed and solid lines indicates accurate registration). Again, the retinal blood vessels (and/or other features) shown in the live video image generated by the first imaging system are accurately registered to the same retinal blood vessels (and/or other features) depicted in the guidance image (e.g., an OCT image), though other portions of the fundus images are not registered. Registration system 108 does not attempt to register portions of the first and second images outside registration region 220B.

Hence, by restricting image registration to priority registration regions (e.g., regions 220A and 220B) near tool tip 212, registration system 108 is able to maintain registration with high accuracy and speed even as the tool tip 212 moves, improving responsiveness and system performance.

FIG. 4 also depicts an image of fundus 200 generated by a first imaging system 104 (e.g., a video microscope). Retinal blood vessels in the live video image generated by the first imaging system 104 are depicted as solid black lines, while retinal blood vessels in the guidance image overlay generated by the second imaging system 106 are depicted as dashed lines. Here, registration system 108 receives and analyzes the video image to identify particular retinal features or pathologies, indicated as features 402, 404, and 406, and an optic nerve 408, using feature-based, region-based, or motion-based object tracking algorithms. Priority registration regions 400A, 400B, 400C, and 400D are then defined by registration system 108 to encompass the areas within a particular radial distance of retinal features 402, 404, and 406, and optic nerve 408, respectively. Within these priority registration regions 400A-D, the retinal blood vessels (and/or other features) shown in the video image are quickly and accurately registered to the same retinal blood vessels depicted in the guidance image, as indicated by the alignment of dashed and solid lines. Meanwhile, portions of the images outside priority registration regions 400A-D are not registered. Although multiple registration regions based on different features are shown in FIG. 4 as being simultaneously registered, it should be understood that in various embodiments, a system operator may select which features to track for defining registration regions. For example, registration system 108 may be configured to implement the processes described herein within registration regions 400A-C, but not registration region 400D. Any other suitable configuration may be selected.

FIG. 5 depicts an image of the external structures of an eye 102, including a pupil 502, iris 504, and sclera 506, generated by a first imaging system 104 (e.g., a video microscope). In this example, registration system 108 receives and analyzes the image to identify features of interest such as particular vessels of sclera 506 or visible patterns on iris 504 using feature-based, region-based, or motion-based object tracking algorithms. This process may be executed in real time to dynamically identify and track these features. Registration system 108 then defines priority registration regions 500A and 500B to encompass the areas within a particular radial distance of scleral vessels. Priority registration region 500C is defined to encompass the entire iris 504. Priority registration region 500D is defined to encompass an area surrounding a particular pattern identified on iris 504. Although not depicted in FIG. 5, it is understood that the identified feature may be the location of a tool tip, as discussed above with respect to FIG. 3. As in the examples discussed with respect to FIGS. 3 and 4, video and guidance images of iris and scleral features within priority registration regions 500A, 500B, 500C, and 500D are registered with high accuracy and speed. Accurate registration within regions 500A, 500B, and 500D is indicated by the alignment of dashed and solid lines. Within region 500C, it should be understood that the video and guidance images are fully and accurately registered, though this is not shown with dotted lines for the sake of clarity. Although multiple registration regions based on different features are shown in FIG. 5 as being simultaneously registered, it should be understood that in various embodiments, a system operator may select which features to track for defining registration regions. For example, registration system 108 may be configured to implement the processes described herein within registration region 500C, but not registration regions 500A, 500B, or 500D. Any other suitable configuration may be selected.

Thus, embodiments of the disclosure improve the speed and accuracy of image registration in critical areas of the image with an adaptive registration system that prioritizes registration of, and limits image registration to, high-priority areas in a surgical field-of-view. In this manner, image registration system 108 can increase processing resources dedicated to continuously registering and updating the portions of the image that are most critical to a surgical procedure. This can improve the accuracy and reliability of the images displayed to surgeons, and may in certain embodiments be implemented as a software upgrade in conventional systems without modifications to hardware.

It will be appreciated that several of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. An ophthalmic imaging system, comprising:
   a first imaging system configured to generate a first image of an eye;
   a second imaging system configured to generate a second image of the eye;
   an image registration system comprising a processor and instructions stored on a memory, the instructions executable by the processor to cause the image registration system to:
      receive the first image generated by the first imaging system;
      receive the second image generated by the second imaging system;
      track a location of a distal tip of a surgical instrument in the first image;
      define a priority registration region in the first image, the priority registration region comprising a portion of the first image within a predetermined proximity of the distal tip of the surgical instrument;
      register the priority registration region in the first image with a corresponding region in the second image; and
      update registration of the priority registration region in the first image with the corresponding region in the second image in real time as the distal tip is moved, without registering portions of the first and second images that are outside the priority registration regions, wherein a size of the priority registration region is dynamically increased or decreased as necessary to maintain a desired performance in the priority registration region as a processing load varies.

2. The ophthalmic surgical system of claim 1, wherein the first and second images comprise first and second images of a fundus, a sclera, or an iris.

3. The ophthalmic surgical system of claim 2, wherein the first imaging system comprises at least one of a surgical microscope, a 2-dimensional camera, a line-scan camera, and a single detector as used in a confocal scanning ophthalmoscope.

4. The ophthalmic surgical system of claim 3, wherein the second imaging system comprises at least one of an Optical Coherence Tomography (OCT) imaging system and a fluorescein angiogram imaging system.

5. The system of claim 4, further comprising instructions executable by the processor to cause the image registration system to generate, in real time, a display image in which:
   the priority registration region in the first image is aligned with the corresponding priority registration region in the second image; and
   portions of the first or second images that are outside the priority registration regions are not registered.

6. The system of claim 5, wherein an unregistered portion of the first or second image is visually suppressed in the generated display image.

7. The ophthalmic surgical system of claim 5, further comprising an eyepiece or a heads-up screen configured to display the generated display image.

8. The ophthalmic surgical system of claim 5, wherein at least one characteristic of the priority registration region is configurable by a user.

9. The ophthalmic surgical system of claim 8, wherein a size of the priority registration region is configurable by a user.

10. The ophthalmic surgical system of claim 1, wherein the distal tip comprises a feature of interest selected by a system operator.

11. A method for registering images in an ophthalmic imaging system, comprising:
    receiving a first image of an eye generated by a first imaging system;
    receiving a second image of the eye generated by a second imaging system;
    tracking a location of a distal tip of a surgical instrument in the first image;
    defining a priority registration region in the first image, the priority registration region comprising a portion of the first image within a predetermined proximity of the distal tip of the surgical instrument;
    registering the priority registration region in the first image with a corresponding region in the second image; and
    updating registration of the priority registration region in the first image with the corresponding region in the second image in real time as the distal tip is moved, without registering portions of the first and second images that are outside the priority registration regions, wherein a size of the priority registration region is dynamically increased or decreased as necessary to maintain a desired performance in the priority registration region as a processing load varies.

12. The method of claim 11, further comprising generating, in real time, a display image in which:
    the priority registration region in the first image is aligned with the corresponding priority registration region in the second image; and
    portions of the first or second images that are outside the priority registration regions are not registered.

13. The method of claim 12, further comprising visually suppressing an unregistered portion of the first or second image.

14. The method of claim 12, further comprising displaying the display image in an eyepiece or on a heads-up screen.

15. The method of claim 11, further comprising defining the priority registration region in the first image based on user input.

16. The method of claim 1, further comprising receiving, from a system operator, an input identifying the distal tip as a feature of interest to be tracked.

\* \* \* \* \*